(12) United States Patent
Mantell (10) Patent No.: US 8,257,297 B2
(45) Date of Patent: Sep. 4, 2012

(54) DUAL-CAPACITY INSUFFLATOR TUBE

(75) Inventor: Robert R. Mantell, Arlington Heights, IL (US)

(73) Assignee: Northgate Technologies, Inc., Elgin, IL (US)

( * ) Notice: Subject to any disclaimer, the term of this patent is extended or adjusted under 35 U.S.C. 154(b) by 0 days.

(21) Appl. No.: 12/315,011

(22) Filed: Nov. 26, 2008

(65) Prior Publication Data

US 2009/0082718 A1    Mar. 26, 2009

Related U.S. Application Data

(63) Continuation of application No. 10/696,675, filed on Oct. 28, 2003, now abandoned.

(60) Provisional application No. 60/421,662, filed on Oct. 28, 2002.

(51) Int. Cl.
*A61M 13/00* (2006.01)
(52) U.S. Cl. ............................. 604/26; 604/23
(58) Field of Classification Search .......... 604/23, 604/26, 94.01; 600/560
See application file for complete search history.

(56) References Cited

U.S. PATENT DOCUMENTS

| | | | |
|---|---|---|---|
| 3,853,105 A | 12/1974 | Kenagy | |
| 3,858,572 A | 1/1975 | Binard et al. | |
| 4,048,992 A | 9/1977 | Lindermann et al. | |
| 4,109,656 A | 8/1978 | Goethel et al. | |
| 4,464,169 A * | 8/1984 | Semm | 604/26 |
| 4,676,774 A | 6/1987 | Semm et al. | |
| 4,715,372 A * | 12/1987 | Philippbar et al. | 606/2 |
| 4,878,894 A | 11/1989 | Sutter, Jr. et al. | |
| 4,884,565 A | 12/1989 | Cocozza | |
| 4,895,562 A | 1/1990 | Lopez | |
| 5,013,294 A | 5/1991 | Baier | |
| 5,152,745 A | 10/1992 | Steiner et al. | |
| 5,246,419 A * | 9/1993 | Absten | 604/26 |
| 5,250,287 A | 10/1993 | Cocozza | |
| 5,292,304 A | 3/1994 | Mantell et al. | |
| 5,328,458 A | 7/1994 | Sekino et al. | |
| 5,360,396 A | 11/1994 | Chan | |

(Continued)

FOREIGN PATENT DOCUMENTS

EP    0 369 764 B1    6/1994

(Continued)

OTHER PUBLICATIONS

International Search Report issued in international application No. PCT/US03/31524, dated Oct. 19, 2004 (3 pages).

*Primary Examiner* — Laura Bouchelle
(74) *Attorney, Agent, or Firm* — Brinks Hofer Gilson & Lione (57) ABSTRACT

An insufflation system is provided that includes an insufflator having a delivery assembly for delivering insufflating gas from a pressurized source of insufflation gas to at least one gas delivery path. At least one output line is coupled to the at least one gas delivery path. At least one dual-capacity tube has a first tube with a first end coupled to the at least one output line and a second end. The dual-capacity tube has a pair of tubes that each has a first end attached with the second end of the first tube. The dual-capacity tube provides for fluid communication of the insufflating gas between the insufflator and laparoscopic equipment that is insertable into a peritoneal cavity.

8 Claims, 8 Drawing Sheets

U.S. PATENT DOCUMENTS

| | | | |
|---|---|---|---|
| 5,362,310 | A | 11/1994 | Semm |
| 5,363,839 | A | 11/1994 | Lankford |
| 5,411,474 | A | 5/1995 | Ott et al. |
| 5,411,988 | A | 5/1995 | Bockow et al. |
| 5,439,441 | A | 8/1995 | Grimsley et al. |
| 5,464,008 | A | 11/1995 | Kim |
| 5,464,144 | A | 11/1995 | Guy et al. |
| 5,474,533 | A | 12/1995 | Ward et al. |
| 5,478,837 | A | 12/1995 | Rodgers et al. |
| 5,497,934 | A | 3/1996 | Brady et al. |
| 5,503,320 | A | 4/1996 | Webster et al. |
| 5,514,087 | A | 5/1996 | Jones |
| 5,515,860 | A | 5/1996 | Aviv et al. |
| 5,534,261 | A | 7/1996 | Rodgers et al. |
| 5,537,993 | A | 7/1996 | Reichert et al. |
| 5,549,546 | A | 8/1996 | Schneider et al. |
| 5,558,668 | A | 9/1996 | Lankford et al. |
| 5,578,305 | A | 11/1996 | Franz et al. |
| 5,586,974 | A | 12/1996 | Martinez et al. |
| 5,599,297 | A | 2/1997 | Chin et al. |
| 5,676,155 | A | 10/1997 | Novak et al. |
| 5,722,962 | A | 3/1998 | Garcia |
| 5,800,381 | A | 9/1998 | Ognier |
| 5,814,012 | A | 9/1998 | Flennor et al. |
| 5,857,999 | A | 1/1999 | Quick et al. |
| 5,873,819 | A | 2/1999 | Koch |
| 5,908,402 | A | 6/1999 | Blythe |
| 5,972,020 | A | 10/1999 | Carpentier et al. |
| 6,004,509 | A | 12/1999 | Dey et al. |
| 6,036,655 | A | 3/2000 | Aviv et al. |
| 6,042,573 | A | 3/2000 | Lucey |
| 6,051,241 | A | 4/2000 | Briend et al. |
| 6,068,609 | A | 5/2000 | Ott et al. |
| 6,139,519 | A | 10/2000 | Blythe |
| 6,165,201 | A | 12/2000 | Sawhney et al. |
| 6,203,519 | B1 * | 3/2001 | Fagerstrom et al. ............ 604/26 |
| 6,258,069 | B1 | 7/2001 | Carpentier et al. |
| 6,299,592 | B1 | 10/2001 | Zander |
| 6,379,373 | B1 | 4/2002 | Sawhney et al. |
| 6,428,500 | B1 | 8/2002 | Koninckx |
| 2002/0059933 | A1 | 5/2002 | Jaffe et al. |
| 2002/0183715 | A1 | 12/2002 | Mantell et al. |
| 2004/0153027 | A1 | 8/2004 | Mantell |

FOREIGN PATENT DOCUMENTS

| | | |
|---|---|---|
| EP | 0 712 635 B1 | 5/2003 |
| WO | 94/00484 | 1/1994 |
| WO | 96/29987 | 10/1996 |
| WO | 96/40090 | 12/1996 |

* cited by examiner

DUAL-CAPACITY INSUFFLATOR TUBE

This application is a continuation of prior application Ser. No. 10/696,675, filed Oct. 28, 2003, now abandoned which claims the benefit of U.S. Provisional Application No. 60/421,662, filed Oct. 28, 2002, the entirety of which is incorporated by reference.

FIELD OF THE INVENTION

The present invention relates to the field of surgical instruments, and in particular, relates to the technology and instrumentation used to achieve pneumoperitoneum during laparoscopy and laparoscopic surgery.

BACKGROUND

Surgeons have used laparoscopic surgery to perform a variety of procedures. By manipulating laparoscopes and video telescopes, surgeons gain a visualization of the abdominal cavity while minimizing tissue and muscle injury that normally accompanies conventional invasive procedures. Compared to conventional surgery, laparoscopy reduces patient trauma, decreases patient recovery time, and yields significant cost savings by reducing post-operative care.

The proper hardware and instrumentation are essential to the performance of laparoscopic procedures. To create a sufficient area for the introduction of a laparoscope and other instruments, the abdominal wall is first raised from the organs enclosed in the abdominal cavity. Separation is conventionally attained by pressurizing the abdominal cavity with an insufflation gas. Typically, carbon dioxide or nitrous oxide is used. The presence of artificial gas in the peritoneal cavity to achieve exposure during laparoscopy is referred to as pneumoperitoneum.

When maintaining pneumoperitoneum, it is desirable on occasion to infuse the insufflation gas into the cavity at a rate typically above 20 liters per minute. Achieving this rate, however, often is difficult. One of the primary limitations in providing higher flows of insufflation gas are the constraints placed upon the insufflation equipment by both common industry practice, efficacy requirements, and guidance documents issued by the United States Food and Drug Administration concerning issues such as push pressures, pressure duration, overshoot, and pressure relief. Insufflators normally are limited to a push pressure of about 45 to 55 millimeters of mercury. This limitation makes it very difficult to infuse insufflation gas at the desired higher flow rates. Furthermore, the equipment associated with laparoscopic procedures, including the use of standard single PVC tubing, sub-micron filters, and standard laparoscopic equipment such as fixed and rotating collar luers, verres needles, and trocars further restrict the infusion rate of the insufflation gas.

Several techniques have been used to attempt to overcome these limitations. One technique is to use an insufflator with two separate supply sources of insufflating gas, with each providing up to 20 liters or more of flow per minute. This type of insufflator allows high flow rates to be provided so that pneumoperiteum may be maintained. This type of insufflator, however, requires an insufflator capable of creating and controlling separate flow paths within the insufflator, and as a result increases the costs and complexity associated with the insufflator.

Another approach has been to create very large, low restriction paths within an insufflator, large output lines on the front of the insufflators. This type of insufflator, however, requires the use of much larger, non-standard tubing. Also, non-standard, large-opening, expensive trocars and or verres needles are required. Presently, these are not readily available or are not disposable as are the instruments currently in use.

Accordingly, it is desirable to have a device that overcomes the disadvantages and limitations described above.

BRIEF SUMMARY

In order to address the need for an improved apparatus to provide a higher flow rate of insufflation gas, a novel insufflation system is described below. The insufflation system includes an insufflator having a delivery assembly for delivering insufflating gas from a pressurized source of insufflation gas to at least one gas delivery path. At least one output line is coupled to the at least one gas delivery path. At least one dual-capacity tube has a first tube with a first end coupled to the at least one output line and a second end. The dual-capacity tube has a pair of tubes that each has a first end attached with the second end of the first tube. The dual-capacity tube provides for fluid communication of the insufflating gas between the insufflator and laparoscopic equipment that is insertable into a peritoneal cavity.

Another aspect of the invention includes a multi-capacity tube. The multi-capacity tube includes a first tube having a first end for attachment to an insufflator and a second end attached to a first end of an adapter. At least two tubes are provided and each has a first end attached to a second end of the adapter and a second end having a connector. A laparoscopic surgical component is attached to the connector on the second end of each of the at least two tubes. The at least two tubes provide pathways for pressurized insufflation gas and the laparoscopic surgical component is insertable into a peritoneal cavity.

Another aspect of the invention includes an insufflation system. The insufflation systems includes an insufflator having a delivery assembly for delivering insufflating gas from a pressurized source of insufflation gas to at least one gas delivery path. At least one output line is coupled to the at least one gas delivery path. At least one multi-capacity tube has a first tube with a first end coupled to the at least one output line and a second end. The multi-capacity tube has at least two tubes that each has a first end attached with the second end of the first tube and a second end. At least one spike port is attached with the second end of one of the at least two tubes. The spike port prevents the flow of insufflation gas through the attached one of the at least tube tubes until the at least one spike port is opened. The multi-capacity tube provides for fluid communication of the insufflating gas between the insufflator and laparoscopic equipment that is insertable into a peritoneal cavity.

An alternate aspect of the insufflation system includes an insufflator having a delivery assembly for delivering insufflating gas from a pressurized source of insufflation gas. At least one multi-capacity tube having a first tube with a first end is coupled to the delivery assembly and a second end. The at least one multi-capacity tube has at least two tubes each having a first end attached with the second end of the first tube. At least two outputs are each coupled to a second end of the at least two tubes of the multi-capacity tube.

Another aspect of the invention includes a method for delivering insufflation gas to a peritoneal cavity. The method includes providing a source of insufflation gas to an insufflator. A first end of a multi-capacity tube is attached to at least one port of the insufflator. The multi-capacity tube has at least two second ends having laparoscopic equipment attached to each of the at least two second ends. The laparoscopic equipment attached to the at least two second ends of the multi-capacity tube is inserted into the peritoneal cavity. The insufflation gas flows from the gas source, through the insufflator and through the multi-capacity tube to the peritoneal cavity.

DETAILED DESCRIPTION OF THE PRESENTLY PREFERRED EMBODIMENTS

Figure 1:
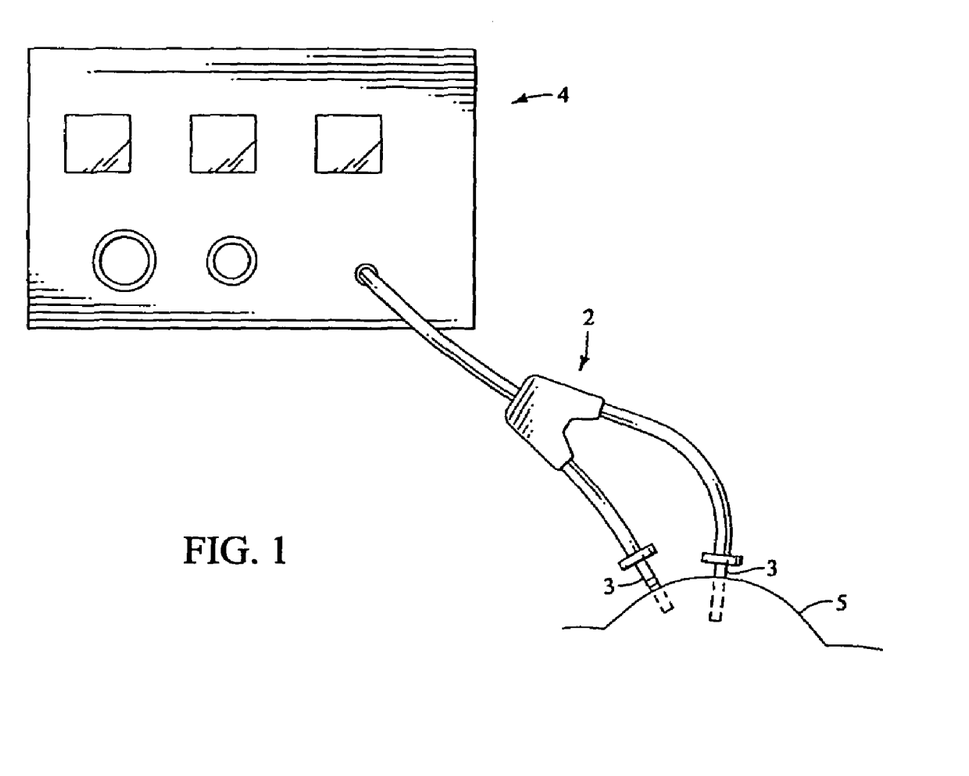
FIG. 1 is a view of a first embodiment of a dual-capacity tube and an insufflator.
Figure 2:
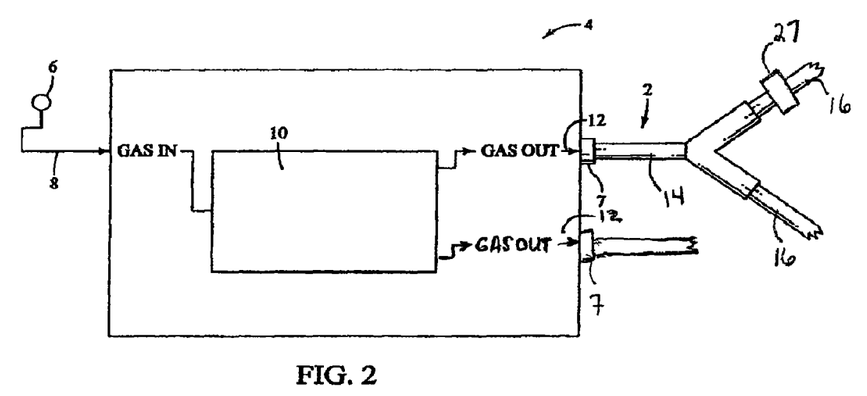
FIG. 2 is a view of the insufflator of FIG. 1.

Referring to FIGS. 1 and 2, an embodiment of a dual-capacity tube 2 attached to an insufflator 4 is shown. As will be discussed further below, the dual-capacity tube 2 provides for the fluid communication of an insufflating gas between the insufflator 4 and laparoscopic equipment 3 that is inserted into a peritoneal cavity 5.

The insufflator 4 is a standard insufflator, such as the OMNIFLATOR Model 6620 available from Northgate Technologies, Inc. in Elgin, Ill. The insufflator 4 includes a pressurized source 6 of insufflation gas 8. Examples of insufflation gases 8 include, but are not limited to, carbon dioxide, nitrous oxide, argon, or helium. The insufflation gas 8 is reduced in pressure by the insufflator to approximately 45 through 55 millimeters of mercury (also known as a "push" pressure), although the pressure may be changed depending on the insufflator in use and any regulations that may be in force. The insufflation gas 8 is delivered via a delivery assembly 10 to at least one output line 12 and passes from the insufflator 4 to the dual-capacity tube 2. The dual-capacity tube 2 connects to a port 7 associated with the output line 12 of the insufflator 4. The delivery assembly 10 is mainly comprised of electronics and pneumatics which, as noted above, are standard to the insufflator 4.

Figure 3:
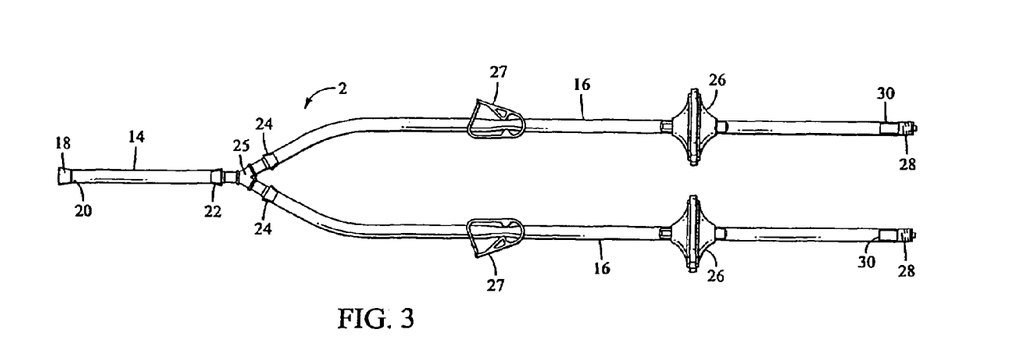
FIG. 3 is a view of the dual-capacity tube of FIG. 1.

Referring to FIG. 3, the dual capacity tube 2 includes a first tube 14 and a pair of tubes 16 attached to the first tube 14. A connector 18 on a first end 20 of the first tube 14 is attached to the output line 12 of the insufflator 4 via the port 7. Any suitable connector 18 may be used, but the connector 18 should be of a type so the flow capacity of insufflation gas 8 from the output line 12 is not restricted. Examples of connectors include, but are not limited to, barb, spring-loaded, or quick-disconnect connectors. A second end 22 of the first tube 14 is attached to a first end 24 of each of the pair of tubes 16 via an adapter 25. Although a stepped adapter, also referred to as a barbed adapter, is contemplated for use with the present embodiment, in other embodiments any suitable adapter may be used such as a tapered connector allowing for a "pressed" or bonded fit.

A connector 28 is attached to a second end 30 of each of the pair of tubes 16. As with the connector 18 associated with the first end 20 of the first tube 14, the connector 28 should be of a type so the flow capacity of insufflation gas 8 from the output line 12 is not restricted. An example of a suitable connector is a luer connector. The connectors 28 on the second end 30 are for attachment with either laparoscopic equipment 3 or additional dual-capacity tubes 2. Examples of laparoscopic equipment 3 for attachment to the connector 28 on the second end 30 include verres needles, trocars, and cannulas.

The tubes 14, 16 of the dual-capacity tube 2 should preferably be made from a flexible material. In the present embodiment, the tubes 14, 16 are disposable polyvinyl chloride tubes, although in other embodiments any suitable materials may be used. For example, the tubing may be made of a silicone material that is reusable. In one embodiment, the first tube 14 has an inner diameter approximately ⅜ inches and the pair of tubes 16 each normally has an inner diameter of approximately ¼ inches. Of course, the diameters of the tubes 14, 16 may be varied depending on flow rate requirements and any regulations that are in force. Moreover, the inner diameter of each of the pair of tubes 16 may be different from each other. To achieve the greatest benefits of a higher flow rate, however, the inner diameter of the first tube 14 should be at least as large as the inner diameter of each of the pair of tubes 16. Moreover, the pair of tubes 16 should be sized so that they are each compatible with the laparoscopic equipment 3. For example, if each of the pair of tubes 16 has too large of an inner diameter, it will require a larger connector 28. If the connector 28 is too large, it will not be compatible with the laparoscopic equipment 3.

Figure 7:
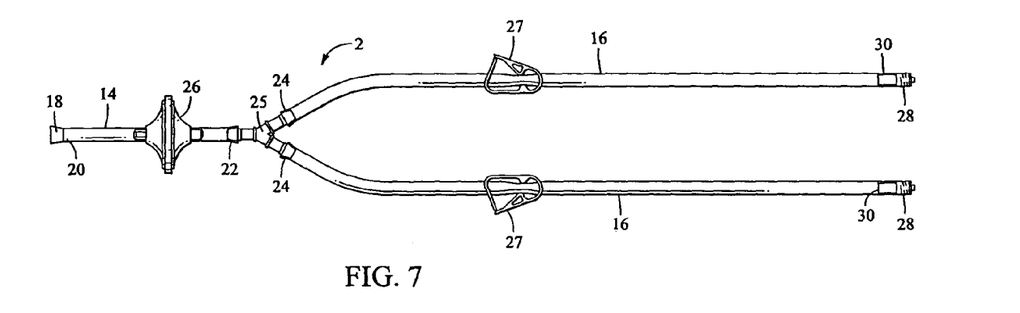
FIG. 7 is a view of an alternate configuration of the dual-capacity tube of FIG. 3.

A filter 26 normally is located in each of the pair 16 of tubes to provide a particulate barrier. Alternatively, however, and as shown in FIG. 7, one filter 26 may be located within the first tube. In one embodiment, the filter 26 is a glass-fiber hydrophobic filter that provides a particulate barrier of approximately 0.2 microns and operates at a ninety-nine percent rate of efficiency. In other embodiments any number of commonly used filters, with different filtering capabilities, may also be used.

A valve 27 is associated with at least one of the pair of tubes 16 and may restrict the flow of insufflation gas 8 in a closed or partially closed state, or may allow the free flow of gas in a fully open state. Although the present embodiment contemplates the valve 27 being located within one of the pair of tubes 16, in other embodiments the valve 27, such as the MEDEX Medical Valve, part no. B15061 LG2, may be located within the connector 28 on the second end 30.

Figure 4:
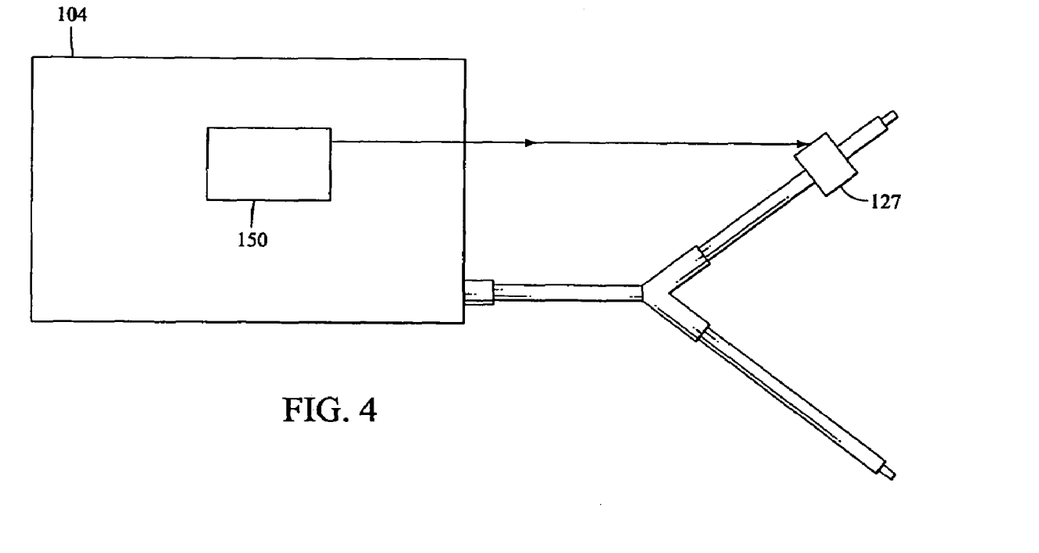
FIG. 4 is a diagram of a second embodiment of an insufflator and dual-capacity tube showing a feedback loop.

Many types of valves may be used. For example, the valve may be a manual valve, or may be operated electrically, pneumatically, or hydraulically. In other embodiments, the valve may be a pressure relief valve. When the pressure of the insufflation gas within the dual-capacity tube reaches a preset pressure, the valve opens and provides pressure relief. In additional embodiments and as shown in FIG. 4, the valve 127 may be operated by a signal generated by a controller 150 associated with the electronics of the insufflator 104. An example of such a controller is contained within the control circuitry of the Northgate OMNIFLATOR 6620 Insufflator, and an example of such a valve is a pinch valve. The signal is generated via feedback due to the monitoring of flow restriction or back pressure sensed by the controller 150. The monitoring of the pressure of the insufflation gas is accomplished via a pressure transducer (not shown) in the controller 150 that monitors the pressure in the dual-capacity tube 2.

As noted above, the dual-capacity tube provides for the flow of pressurized insufflation gas that exits from the insufflator. Each of the second ends 30 has a connector 28 for the attachment of laparoscopic equipment 3 for insertion into a peritoneal cavity 5. The cavity 5 is then inflated with the insufflation gas 8 flowing through the dual-capacity tube 2.

When laparoscopic surgery is being performed, normally it is desirable to have insufflation gas infused into the cavity at a higher rate, with 20 or more liters per minute being preferred. Typically, this gas is infused into the cavity using a standard single tube. Often, it is difficult to achieve this infusion rate using standard single tubes because of the limited push pressure provided by the insufflator. Moreover, as noted above, the tube should be of a size so that it is compatible with laparoscopic equipment. Generally, the laparoscopic equipment currently available limits the flow rate of insufflation gas into a cavity to approximately 10-15 liters per minute.

Because of its configuration, the dual-capacity tube provides an inexpensive solution for facilitating a higher flow rate of insufflation gas. For example, the larger first tube 14 may be of a size to allow insufflation gas 8 to flow at approximately 20 or more liters per minute. The presence of the pair of tubes 16, each sized to be compatible with laparoscopic equipment, will each normally allow approximately 10-15 liters per minute of insufflation gas to flow through the laparoscopic equipment and into the cavity. The presence of a pair of tubes thus provides for a total flow rate of 20 or more liters of insufflation gas per minute. In other embodiments, where the tubes are of a different size or a different flow rate is desired, the dual-capacity tube provides for a higher rate of flow in a similar manner.

Figure 5:
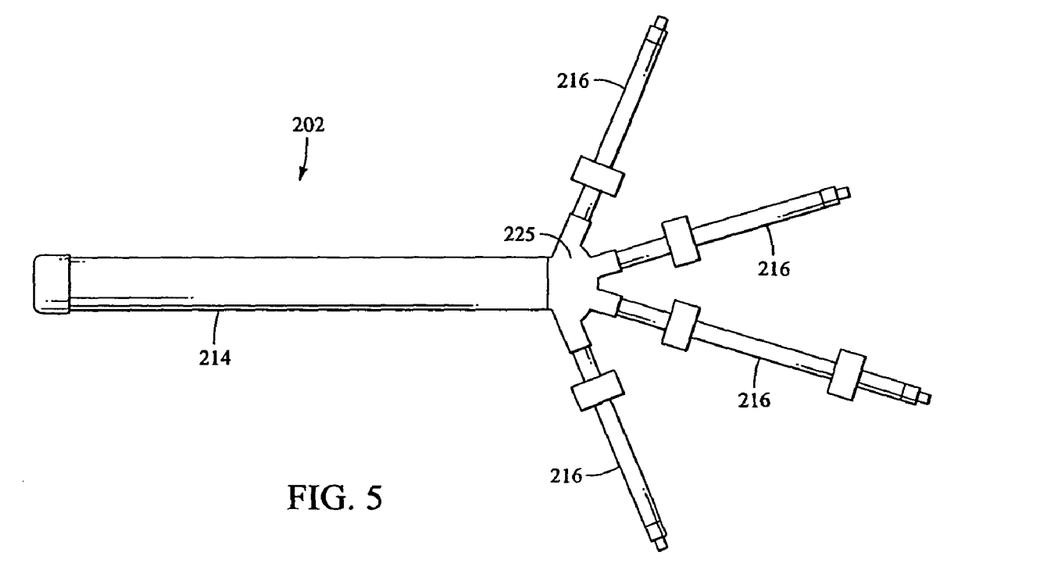
FIG. 5 is a view of a multi-capacity tube.

FIG. 5 shows an additional embodiment of the dual-capacity tube. A multi-capacity tube 202 is shown. As with the embodiment shown in FIG. 3, the multi capacity tube has a first tube 214 for attachment to an insufflator 104. This embodiment, however, includes a plurality of tubes 216 attached to the first tube 214 via an adapter 225. The inner diameter of the tubes 214, 216 should be similar to the sizes described above. Connectors, valves and other equipment are also associated with the multi-capacity tube and are the similar to those described for the dual-capacity tube above. A higher flow rate is provided for with the multi-capacity tube in a manner similar to the example given above for the dual-capacity tube.

In addition to attaching laparoscopic equipment, additional dual-capacity tubes 2 or multi-capacity tubes 202 may also be attached to the connector 28 on the second end 30 of at least one of the pair of tubes 16. Thus, an additional embodiment is contemplated that provides for a multi-capacity tubing configuration. Moreover, additional dual-capacity tubes or multi-capacity tubes may be attached to the multi-capacity tube associated with FIG. 5.

Figure 6:
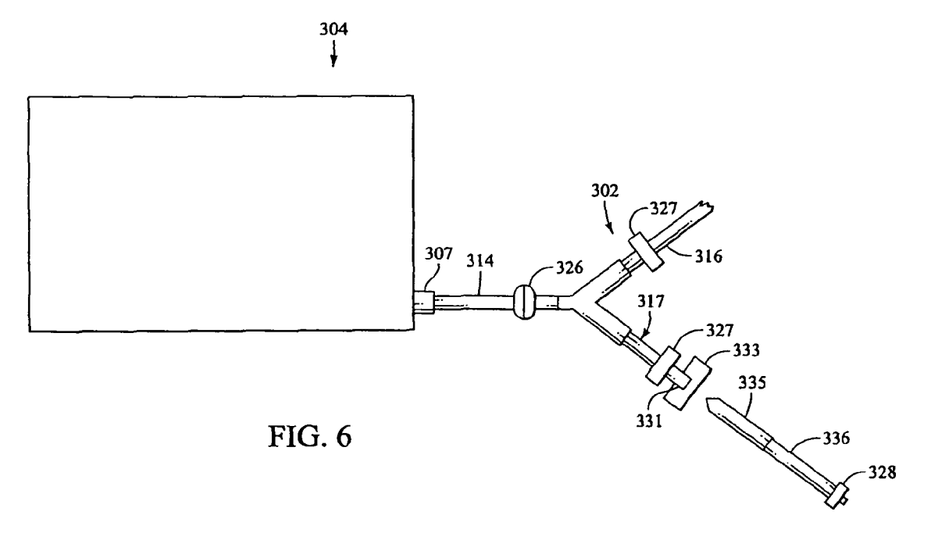
FIG. 6 is a view of an alternate configuration of the dual-capacity tube and the insufflator of FIG. 1.

FIG. 6 shows an additional configuration of a dual capacity tube 302 and insufflator 304 to provide a higher infusion rate of gas into a cavity. The dual-capacity tube is similar to the configuration associated with FIG. 3, except that one of the pair of tubes 316 is a "stub" tube 317. The stub tube 317 may be sized with respect to the other of the pair of tubes 316 and the first tube 314 as described above. A spike port 333 is connected with a second end 331 of the stub tube 317. The other of the pair of tubes 316 is configured as described above and may have a valve 327 associated with it. As in the embodiment in FIG. 3, the first tube 314 is attached to the port 307 of the insufflator 304. The spike port 333 essentially seals the stub tube 317 and prevents the flow of insufflation gas from passing out of the stub tube 317. When a greater flow rate is desired, i.e., when it is desired to have insufflation gas passing through both of the pair of tubes 316, a spike 335 may be used to pierce the spike port 333 of the stub tube 317. The spike 335 has a spike tube 336 connected with it. The spike tube 336 preferably has a connector 328 associated with it for the attachment of laparoscopic equipment. The spike 335 has an internal through-path passing through it to allow the passage of insufflation gas from the stub tube 317 into the spike tube 336.

As with the embodiments described above, a filter 326 may be located within the first tube 314. Alternatively, a filter may be located within the stub tube or the spike tube and the other of the pair of tubes. In addition, the stub tube 317, the spike tube 336, or the connector 328 associated with the spike tube may also contain a valve 327 as described above.

Although the embodiment associated with FIG. 6 utilizes a dual-capacity tube, other embodiments may use a multi-capacity tube that utilizes at least one stub tube. Furthermore, additional dual-capacity or multi-capacity tubes may be attached to any dual-capacity or multi-capacity tubes that are being used with the insufflator in the manner described above.

Figure 8:
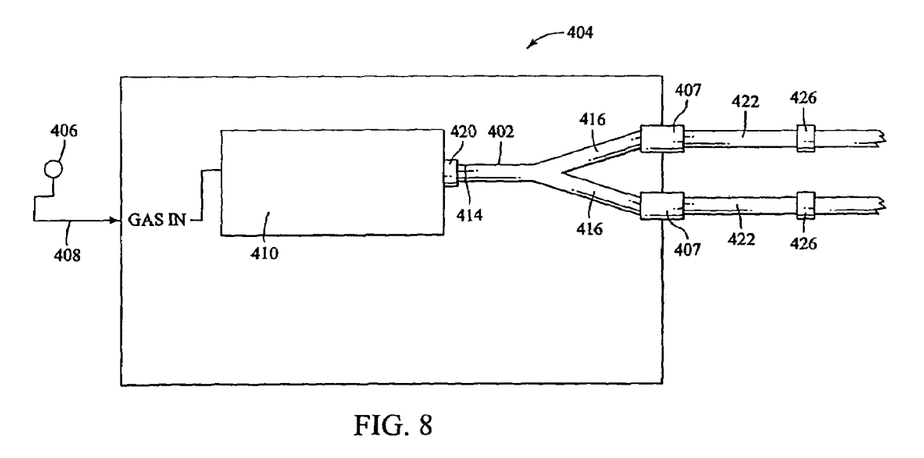
FIG. 8 is a view of an additional embodiment of a dual-capacity tube and an insufflator.

FIG. 8 shows an additional configuration of a dual-capacity tube 402 and insufflator 404. The insufflator 404 is the standard insufflator described above in connection with FIG. 2, such as the OMNIFLATOR Model 6620 available from Northgate Technologies, Inc. in Elgin, Ill., except that it has been slightly modified in as follows: a delivery port 420 has been added to the delivery assembly 410, and an additional output port 407 has been added so that there are now two output ports 407. As described above, the insufflator 404 includes a pressurized source 406 of insufflation gas 408. In this embodiment, the dual-capacity tube 402 is connected within the insufflator 404 so that the first tube 414 is connected to the delivery port 420 associated with the delivery assembly 410 and the pair of tubes 416 is each connected to an output port 407. A pair of delivery tubes 422 each having a filter 426 is attached to an output port 407. The insufflation gas 408 is delivered via the delivery assembly 410 to the dual-capacity tube 402 to the delivery tubes 424. Laparoscopic equipment (not shown) may then be attached to each delivery tube in the manner described above. Thus, a single-output insufflator may now provide two outputs for the delivery of insufflation gas.

In alternate embodiments, additional delivery ports and corresponding output ports may be added to the insufflator so that additional dual-capacity tubes and delivery tubes may be attached. Moreover, although the embodiment associated with FIG. 8 utilizes a dual-capacity tube, other embodiments may use a multi-capacity tube. Furthermore, additional dual-capacity or multi-capacity tubes may be attached to the delivery ports in the manner described above.

The tubing and ports associated with FIG. 8 are the same as those described with the embodiments above. Additionally, filters may be attached to the dual-capacity tube in the ways described above either in lieu of or in addition to the filters associated with the delivery tubes.

The embodiments of the dual-capacity tube described above are used as follows: The dual-capacity tube is attached to at least one port of an insufflator. Laparoscopic equipment such as verres needles, trocars, or cannulas are attached to the ends of the of the dual-capacity tube opposite the end attached to the insufflator. The laparoscopic equipment is then inserted into a peritoneal cavity. Insufflation gas is provided from a gas source to the peritoneal cavity via the insufflator and dual-capacity tube. Note that in embodiments where the dual-capacity tube is internal to the insufflator, delivery tubing is attached to at least two output ports of the insufflator. Laparoscopic equipment, such as that described above, is attached to an end of the delivery tubing opposing the end attached to the insufflator for insertion into the peritoneal cavity. In further embodiments, a multi-capacity tube may be utilized in a manner similar to those described above.

While the above description constitutes the presently preferred embodiments of the invention, it will be appreciated that the invention is susceptible of modification, variation, and change without departing from the proper scope and fair meaning of the accompanying claims.

The invention claimed is:

1. An insufflation system comprising:
   an insufflator having a delivery assembly for delivering insufflating gas from a pressurized source of insufflation gas to at least one gas delivery path, the gas delivery path including at least one output, the gas delivery path including at least one multi-capacity tube positioned external to the insufflator;
   wherein the at least one multi-capacity tube has a first tube with a first end coupled to the gas delivery path output and a second end connected with at least two second tubes in fluid communication with the first tube, each of the at least two second tubes providing for the communication of insufflating gas between the delivery assembly and laparoscopic equipment that is insertable into a peritoneal cavity;
   a valve associated with each second tube for controlling the flow of insufflating gas; and
   wherein an inner diameter of the first tube is greater than an inner diameter of each of the second tubes, and the second tubes are sized to provide a total flow rate of at least 20 liters per minute of insufflating gas to the peritoneal cavity.

2. The insufflation system of claim 1, wherein each valve operates electrically.

3. The insufflation system of claim 1, wherein each valve operates pneumatically.

4. The insufflation system of claim 1, further comprising at least two delivery lines, each delivery line including a first end coupled to a respective one of the at least two second tubes of the multi-capacity tube and a second end coupled to the laparoscopic equipment for insertion the peritoneal cavity.

5. An insufflator comprising:
   a housing;
   a delivery assembly having at least one output for delivering insufflating gas from a pressurized source of insufflation gas;
   at least one dual-capacity tube positioned external to the housing of the insufflator, the at least one dual-capacity tube having a first tube with a first end coupled to the at least one delivery assembly output and a second end, the at least one dual-capacity tube also having at least two tubes each having an end attached with the second end of the first tube; and
   wherein the at least one dual-capacity tube provides for fluid communication of the insufflating gas to laparoscopic equipment that is insertable into a peritoneal cavity, an inner diameter of the first tube is greater than an inner diameter of each of the at least two tubes, and the at least two tubes are sized to provide a total flow rate of at least 20 liters per minute of insufflating gas to the peritoneal cavity.

6. The insufflator of claim 5, wherein the dual-capacity tube further comprises at least one valve attached to at least one of the at least two tubes, the valve for controlling the flow of insufflation gas.

7. The insufflator of claim 6, wherein the at least one valve is a manual valve.

8. The insufflator of claim 6, wherein the at least one valve operates electrically.

* * * * *